United States Patent [19]
Wong

[11] Patent Number: 5,539,207
[45] Date of Patent: Jul. 23, 1996

[54] METHOD OF IDENTIFYING TISSUE

[75] Inventor: Patrick T. T. Wong, Ottawa, Canada

[73] Assignee: National Research Council of Canada, Ottawa, Canada

[21] Appl. No.: 277,086

[22] Filed: Jul. 19, 1994

[51] Int. Cl.$^6$ ............ G01N 21/85; A61B 5/00; A61B 6/00
[52] U.S. Cl. ............ 250/339.08; 250/339.07; 250/339.09; 250/339.12
[58] Field of Search ............ 250/339.09, 339.12, 250/339.08, 339.07

[56] References Cited

U.S. PATENT DOCUMENTS

| | | |
|---|---|---|
| 5,038,039 | 8/1991 | Wong et al. . |
| 5,168,162 | 12/1992 | Oong et al. . |
| 5,261,410 | 11/1993 | Alfano et al. ............ 128/664 |

FOREIGN PATENT DOCUMENTS

| | | | |
|---|---|---|---|
| 60-98335 | 6/1985 | Japan | ............ 250/339.09 |
| 92/15008 | 9/1992 | WIPO | ............ 250/339.08 |

OTHER PUBLICATIONS

Basil Rigas and Patrick T. T. Wong, "Human Colon Adenocarcinoma Cell Lines Display Infrared Spectroscopic Features of Malignant Colon Tissues." *Cancer Research*, vol. 52 (Jan. 1, 1992) pp. 84–88.

*Primary Examiner*—Constantine Hannaher
*Attorney, Agent, or Firm*—Marks & Clerk

[57] ABSTRACT

A method of identifying tissue involves determining the infrared spectrum of a tissue sample in at least one frequency band, and comparing the infrared spectrum of the sample with a library of stored infrared spectra of known tissue types to find the closest match.

13 Claims, 12 Drawing Sheets

1

METHOD OF IDENTIFYING TISSUE

BACKGROUND OF THE INVENTION

This invention relates to a method and apparatus for identifying tissue, which may be human or animal tissue.

The infrared spectra of the malignant tissue and the normal mucosa of the human colon have been measured. For example, U.S. Pat. No. 5,038,039 described a method of detecting the presence of anomalies in biological tissues and cells in natural and cultured form (e.g. cancerous tissues or cells) is detected by infrared spectroscopy. A beam of infrared light is directed at a sample of tissues or cells in natural or cultured form containing the cells to be tested, and the anomaly is detected at at least one range of frequencies by determining whether changes in infrared absorption have occurred due to the vibration of at least one functional group of molecules present in the sample which is characteristic of the anomaly.

U.S. Pat. No. 5,168,162 describes a method of detecting the presence of anomalies in exfoliated cells using infrared spectroscopy wherein the anomaly is detected in at least one range of frequencies by determining whether changes in infrared absorption has occurred which is due to functional group vibration in, for example, phosphodiester groups of nucleic acids, COH groups of tissue proteins, carbohydrates, or due to special arrangements of lipid molecules or abnormal lipid structures, present in the specimen.

While this approach, i.e. interpreting the changes in the spectra from normal mucosa to malignant tissue in terms of structural changes at the molecular level, is of considerable value, a problem can arise due to the fact that colonic mucosa is composed of glandular epithelium and lamina propria which is mainly loose connective tissue. Malignant tumors of the colon are derived almost exclusively from the epithelium. Therefore, the changes in the spectra may entirely arise from the differences between the connective tissue and the epithelial tissue of the colon and may not be the consequence of the structural changes of the tissue molecules in the pathway of carcinogenesis. Moreover, the spectra of the colon mucosa are very similar to the spectrum of the cervical connective tissue, which indicates that the colonic mucosa samples may be mainly connective tissue and may not contain any epithelium.

SUMMARY OF THE INVENTION

Accordingly, the present invention provides a method of identifying tissue comprising the steps of determining the infrared spectrum of a tissue sample over a range of frequencies in at least one frequency band, and comparing the infrared spectrum of said sample with a library of stored infrared spectra of known tissue types by visual comparison or using pattern recognition techniques to find the closest match. "Infrared Spectrum" is defined herein as a display or graph of the intensity of infrared radiation emitted or absorbed by a material as a function of wavelength or some related parameter.

In accordance with the invention the infrared spectrum is compared with a library of stored data, and from this comparison a positive identification is made. This technique can be applied to the detection of tissue types and malignancies. If the infrared spectrum of a sample matches the stored spectrum of a known normal tissue type, an immediate negative determination can be made.

In order to study the above-noted problems, infrared spectra of the epithelial layer and of the connective tissue from the lamina propria in the human colon have been studied in great detail, and compared with the colonic mucosa. The structural changes at the molecular level from the normal epithelial tissue to the malignant epithelial tissue of the colon have also been determined from their pressure-tuning infrared spectra. These changes represent the true structural changes at the molecular level in this neoplastic transformation.

BRIEF DESCRIPTION OF THE DRAWINGS

The invention will now be described in more detail, by way of example only, with reference to the following examples and accompanying drawings, in which.

DESCRIPTION OF THE PREFERRED EMBODIMENTS

EXAMPLES

Tissue samples were obtained immediately after bowel resection from the Ottawa Civic Hospital and stored at −80° C. until used. Colonic epithelium samples were obtained by scraping or brushing the surface of the mucosa while the connective tissue samples were carefully separated from the mucosa under the microscope. Sections of each tissue sample were stained, and examined histologically.

Infrared spectra were recorded on a BOMEM Michelson 110 Fourier transform spectrometer equipped with a liquid nitrogen cooled mercury-cadmium telluride detector. For each spectrum, 350 scans were coadded at a spectral resolution of 4 $cm^{-1}$. Small amounts (typically 0.1 mg) of tissue were placed at room temperature, together with powdered α-quartz, into a 0.63 mm-diameter hole in a 0.23 mm-thick stainless steel gasket mounted on a diamond anvil cell as disclosed in U.S. Pat. No. 4,970,396, the contents of which are herein incorporated by reference. Pressure at the sample was determined from the 695 $cm^{-1}$ band of α-quartz. Infrared spectra of at least five different parts of each sample were also recorded at atmospheric pressure with an infrared cell of the type described in U.S. Pat. No. 4,980,551, which is herein incorporated by reference. These spectra were used to examine the tissue distribution in each sample and also the reproducibility of the spectra.

Figure 1:
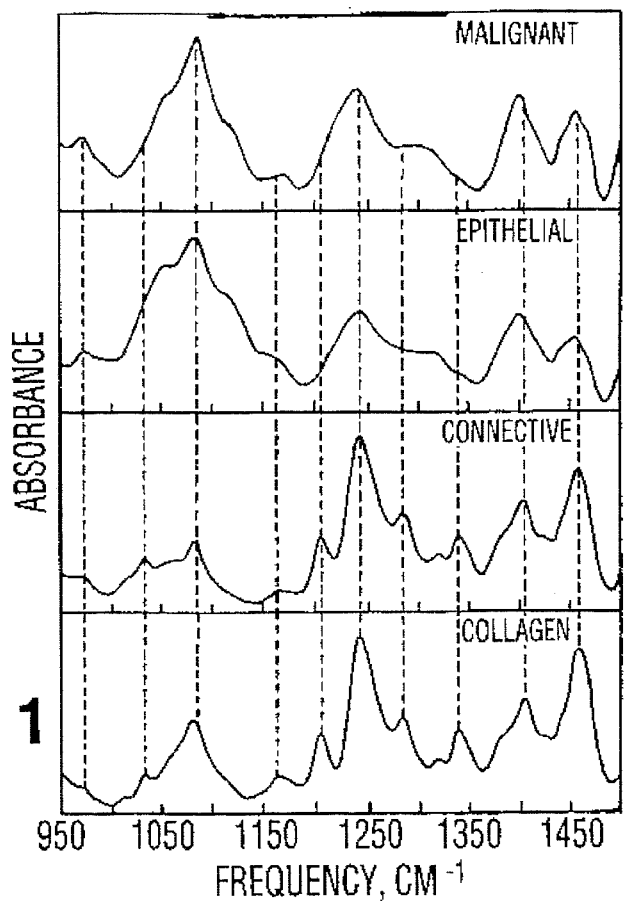
FIG. 1 shows the infrared spectra in the frequency region 950–1500 $cm^{-1}$ of the malignant epithelial, and connective tissues of the colon as well as the type I collagen.

The representative infrared spectra in the frequency region 950 to 1500 $cm^{-1}$ of the epithelial tissue and the connective tissue of the colon were compared with the corresponding malignant epithelial tissue as shown in FIG. 1. One of the basic components in the connective tissues is fibers including collagen fibers, reticular fibers and elastic fibers. Collagen fibers as well as reticular fibers in the connective tissues are formed by protein collagen.

In order to identify the infrared bands and features of collagen proteins in the infrared spectra of the connective tissue, infrared spectra of the type I and type II collagen and elastin protein were measured. The infrared spectrum of the type II collagen was almost the same as that of the type I collagen and the representative infrared spectrum of collagen is shown in FIG. 1.

As evident from FIG. 1, the infrared spectrum of the normal epithelial tissue is significantly different from those of both the normal connective tissue and the malignant epithelial tissue. The spectrum of the connective tissue is similar to the collagen protein especially in the frequency region between 1,150 and 1500 $cm^{-1}$. Therefore the infrared spectrum of the connective tissue is mainly contributed by the spectra of collagen proteins. The band near 1240 $cm^{-1}$ in the connective tissue is stronger than those near 1082 and 1400 $cm^{-1}$ whereas in both the normal and malignant epithelial tissues the 1240 $cm^{-1}$ band is weaker than the 1082 $cm^{-1}$ band but is comparable in intensity with the one near 1400 $cm^{-1}$. The sharp bands at 1030 1204 1283, 1318, and 1339 $cm^{-1}$ in the spectrum of the connective tissue are not present in the spectra of both the normal and the malignant epithelial tissues. They are due to the vibrational modes of the collagen proteins. The intensity of the 1457 $cm^{-1}$ band is higher than the 1400 $cm^{-1}$ band in the connective tissue, whereas the relative intensities of these two bands are reversed in both the normal and the malignant epithelial tissues.

Therefore, infrared spectra in the frequency region from 950 to 1500 $cm^{-1}$ are significantly different between the connective and the epithelial tissues and can be applied unambiguously to identify and differentiate between these two types of colonic tissues.

Figure 2:
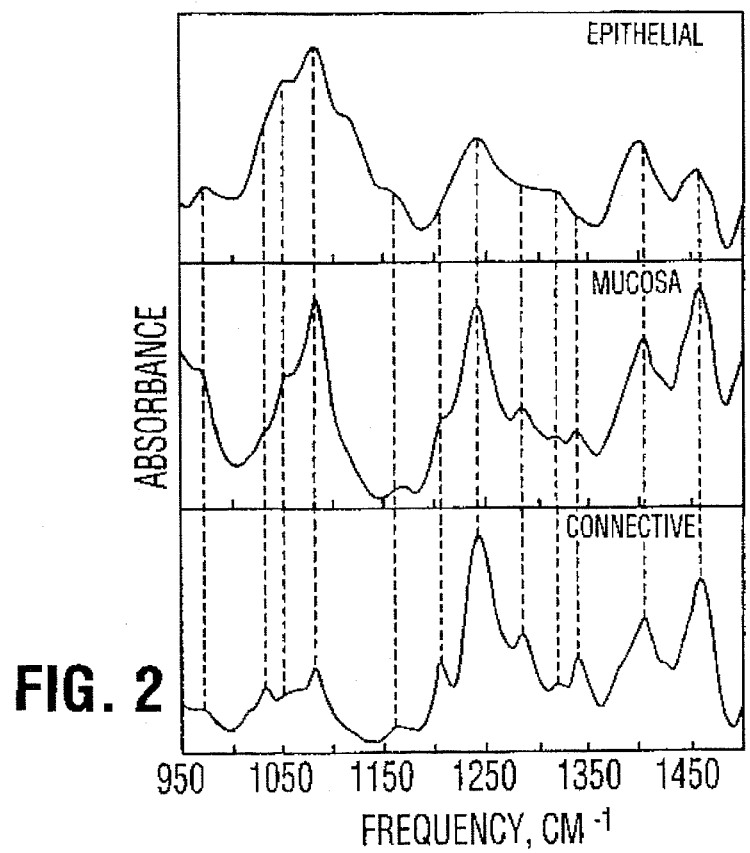
FIG. 2 shows the infrared spectra in the frequency region 950–1500 $cm^{-1}$ of the mucosa, epithelial and connective tissues of the colon.

Mucosa of the colon is composed of glandular epithelium and lamina propria, which is essentially the connective tissue. FIG. 2 compares the infrared spectra of the colonic mucosa, of the connective tissue, and of the epithelial tissue. The infrared spectra of the mucosa represents a combined spectrum from the spectra of the epithelial and the connective tissues. In the spectra of the mucosa the band near 1082 $cm^{-1}$ becomes much stronger than the one in the connective tissue, and its intensity is comparable with the one in the epithelial tissue. On the other hand, the characteristic infrared bands of the connective tissue at 1030, 1204, 1240, 1283, 1318 and 1339 $cm^{-1}$ become much weaker in the spectrum of the mucosa. The infrared spectrum of the colonic mucosa is considerably different from the malignant tissue (FIGS. 1 and 2). This means that the biopsy specimens of the mucosa and the malignant tumor of the colon can be identified and differentiated unambiguously by infrared spectroscopy.

Figure 3:
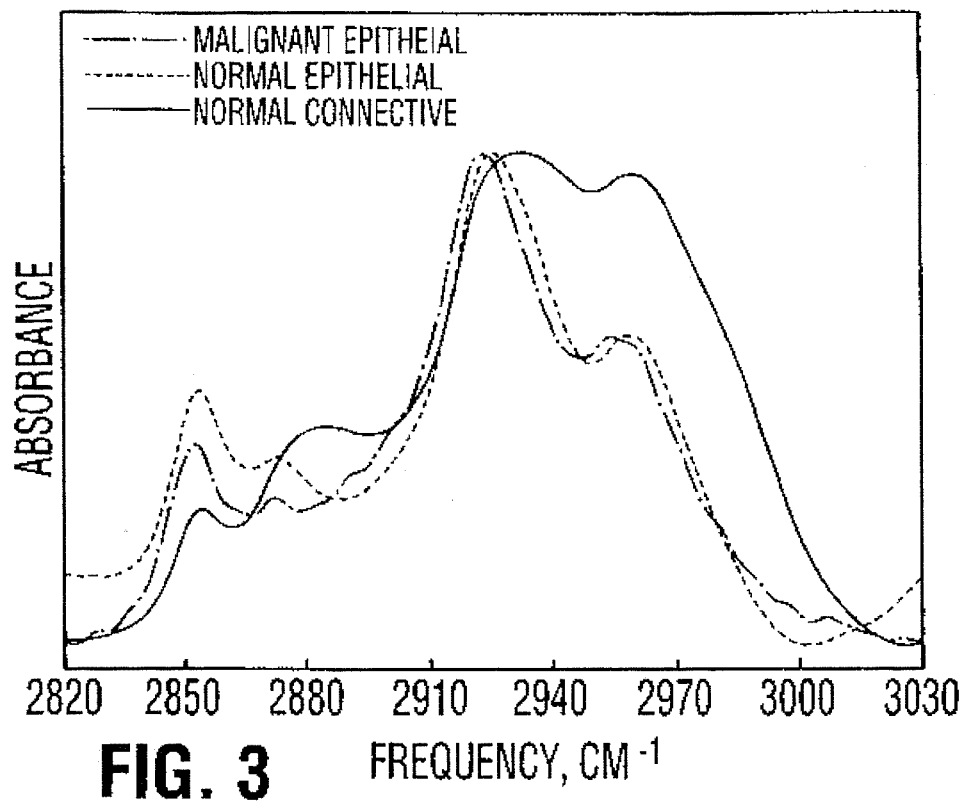
FIG. 3 shows the infrared spectra in the frequency region 2820–3030 $cm^{-1}$ of the malignant, epithelial and connective tissues of the colon.

FIG. 3 shows the infrared spectra in the frequency region 2820–3030 $cm^{-1}$ of the malignant epithelium, normal epithelium, and connective tissue. The peak intensity ratio between the methyl band (2959 $cm^{-1}$) and the methylene band (2853 $cm^{-1}$) decreases slightly from the normal epithelium to the malignant tissues, whereas it increases dramatically in the connective tissue. The decrease in this intensity ratio in the malignant tissue is the result of hypomethylation. The extremely strong methyl band in the connective tissue is mainly contributed from the large number of methyl groups in protein fibers.

Figure 4:
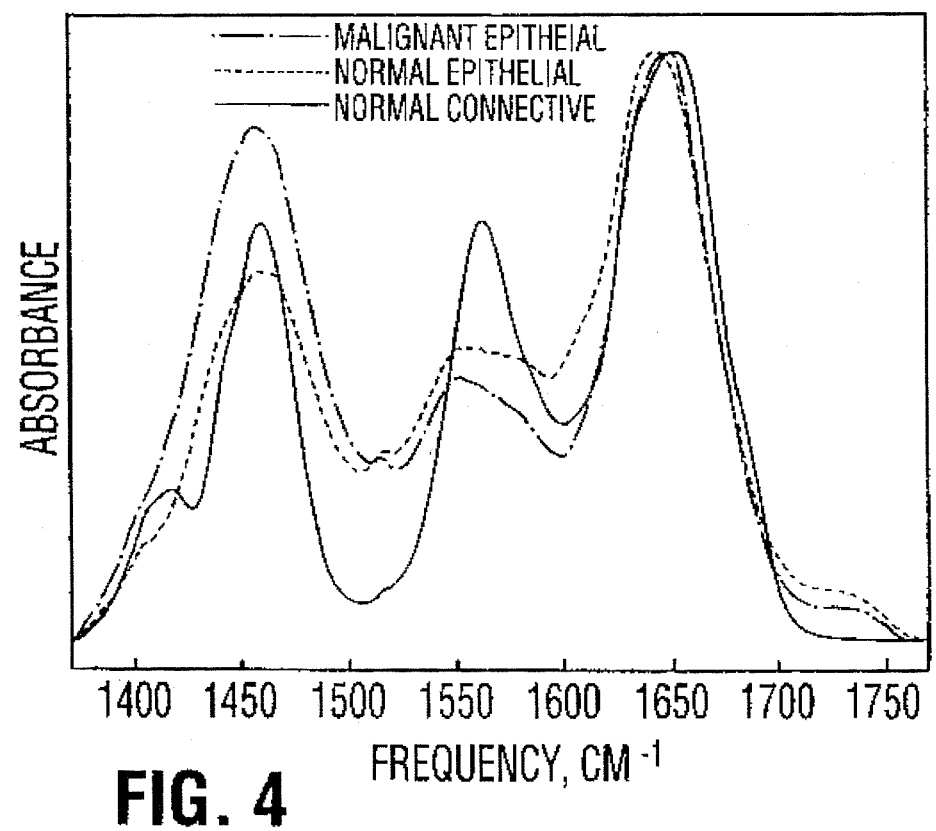
FIG. 4 shows the infrared spectra in the frequency region 1320–1770 $cm^{-1}$ of the malignant, epithelial and connective tissues of the colon.

FIG. 4 shows the representative infrared spectra in the frequency region 1370–1770 $cm^{-1}$ of the three types of colonic tissues. The intensity distribution and the frequency of the amide I band (~1650 $cm^{-1}$) and the amide II band (~1550 $cm^{-1}$) are very sensitive to the conformational substructures in tissue proteins. It is evident from FIG. 4 that both the amide I and the amide II bands are considerably different in the malignant tissue, the normal epithelial tissue and the connective tissue. Therefore, the conformational substructures of tissue proteins in these three types of colonic tissues are expected to differ significantly.

Infrared spectroscopy in combination with high pressure (pressure-tuning infrared spectroscopy) is a powerful method for the study of molecular structure and intermolecular interactions in biological tissues and cells. This has been demonstrated recently by a number of structural and other cellular changes in the malignant cervical tissue and cells derived from pressure-tuning infrared spectroscopic studies. Malignant tumors in the colon are commonly developed from the epithelial cells. Therefore, to investigate the modifications in the molecular structure and intermolecular interactions in the malignant transformation of the colon, it is important that the comparison of these structural properties must be made between the malignant tumor tissue and the normal epithelial tissue.

Figure 5:
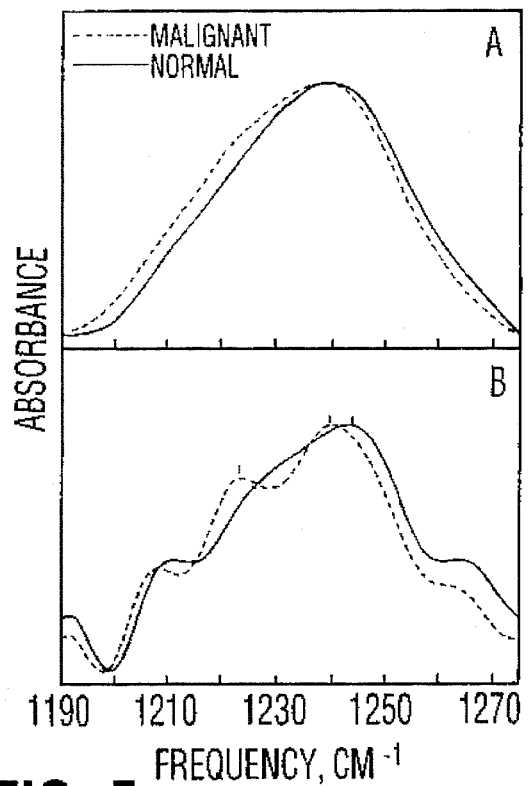
FIG. 5 shows the infrared spectra in the asymmetric phosphate stretching region.; (a) Superimposed original spectra from the malignant and epithelial tissues of the colon. (B) Corresponding deconvolved spectra with an enhancement factor of 1.5 and a band width of 20 $cm^{-1}$.

FIG. 5 shows the enlarged infrared spectra of the asymmetric phosphate stretching band of the phosphodiester groups in nucleic acids from a normal epithelial tissue and a malignant tissue of the colon. Part A shows the original spectra, whereas part B shows the corresponding deconvolved spectra. It is evident from the deconvolved spectra that the asymmetric phosphate stretching band of the colonic tissues consists of two overlapping bands. As observed in the cervical tissues and cells, the frequency of the low-frequency band decreases with increasing pressure due to the hydrogen-bonding on the phosphodiester groups of DNA. The low-frequency component band in the malignant tissue is markedly increased in intensity when compared with the normal tissue. Therefore, in colon cancer many phosphodiester groups of DNA are hydrogen bonded, in contrast to those of the normal epithelial tissue. The frequency of the high frequency component band is about 4 $cm^{-1}$ higher in the normal epithelial tissue than in the malignant tissue, which indicates a different molecular structure of the phosphodiester backbone between these two types of colonic tissues.

The symmetric phosphate stretching band of the phosphodiester groups in the nucleic acids is observed at 1083.9 $cm^{-1}$ in the spectra of the normal epithelial tissue. This frequency is more than 2 $cm^{-1}$ higher in the malignant tissue, which indicates that the intermolecular interactions among nucleic acids in the malignant tissue is stronger as a result of a tighter intermolecular packing. This phenomenon has also been observed in other cancerous tissues and cells.

Figure 6:
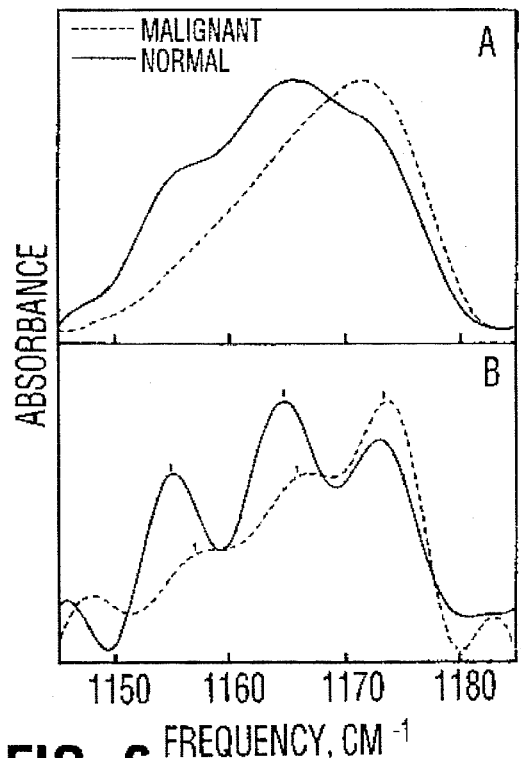
FIG. 6 shows the infrared spectra in the C-O stretching region. (A) Superimposed original spectra from the malignant and epithelial tissues of the colon. (B) Corresponding deconvolved spectra with an enhancement factor of 1.5 and a band width of 10 $cm^{-1}$.
Figure 7:
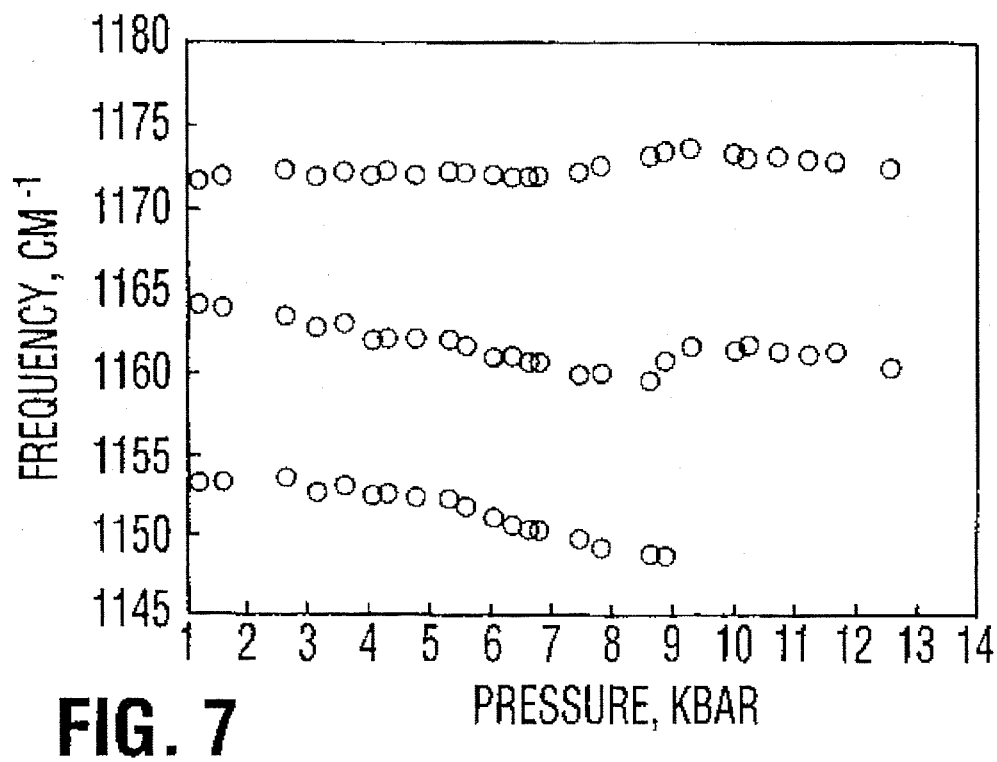
FIG. 7 shows the pressure dependencies of the C-O stretching frequencies of the epithelial tissues of the colon.

Infrared spectra of the C-O stretching bands of the malignant tissues are compared with those of the normal epithelial tissue in FIG. 6. Part A shows the original spectra and Part B shows the deconvolved spectra. This band for both the normal epithelial and the malignant tissues consists of three overlapping bands. Similar to those observed in the cervical tissues and cells, the frequencies of the two low-frequency component bands decrease with increasing pressure (FIG. 7). These results indicate that these two bands are from the hydrogen-bonded C-O groups.

The band at the lowest frequency is due to the stretching mode of the hydrogen-bonded C-O groups from carbohydrates whereas the two bands at the medium and the highest frequency are due to the same mode of the hydrogen-bonded and nonhydrogen-bonded C-O groups, respectively, from tissue proteins. Both the relative intensities and the frequencies of these three component bands in the malignant tissue are considerably different from those of the normal epithelial tissues. Therefore, the relative numbers of hydrogen-bonded to non-hydrogen-bonded C-O groups as well as the environments of the C-O groups are significantly different after the malignant transformation.

Figure 8:
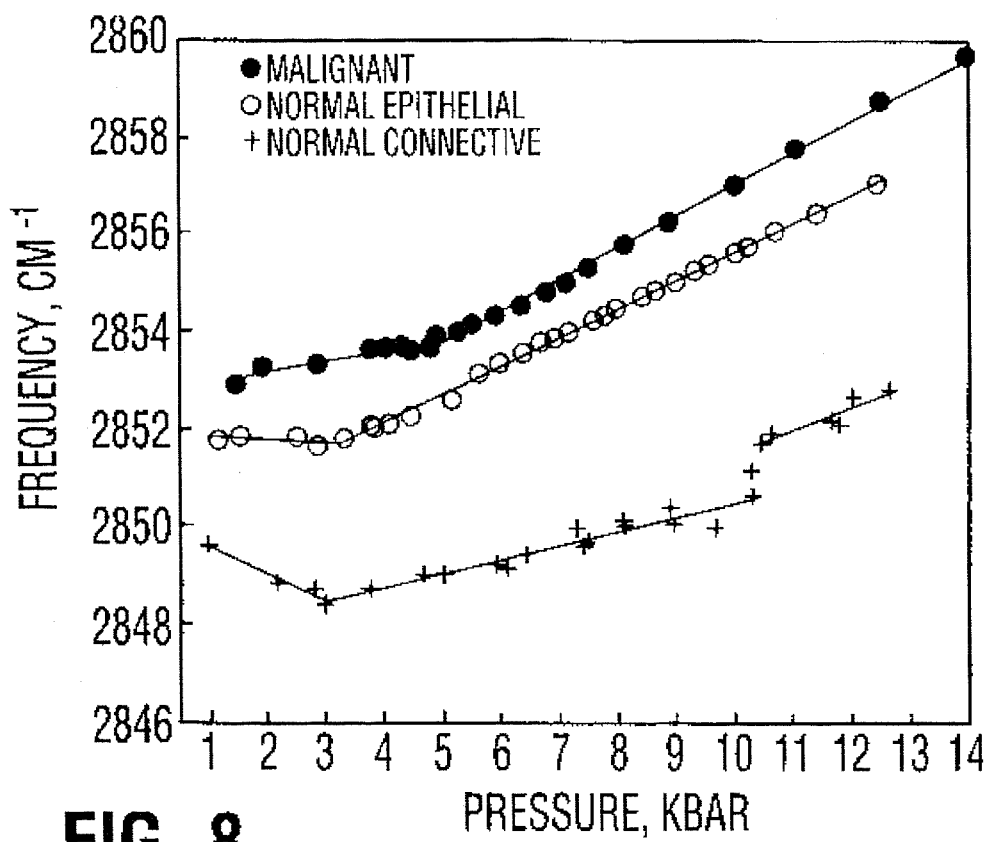
FIG. 8 shows the pressure dependencies of the symmetric $CH_2$ stretching frequencies of the malignant, epithelial and connective tissues of the colon.

The properties of membrane lipids can be monitored by the frequency and its pressure shift of the $CH_2$ stretching and bending modes of the methylene chains in the lipids. The pressure dependencies of the $CH_2$ stretching frequencies of the membrane lipids in the normal epithelial and the malignant tissues of the colon are shown in FIG. 8. The $CH_2$ stretching frequency of the malignant tissue is higher than the normal epithelial tissues. This suggests that the conformational structure of the membrane lipids is more disordered in the malignant tissue than in the normal epithelial tissue. A change of slope in the pressure dependence of the frequency is observed slightly below 5 kbar for the malignant tissue and slightly above 3 kbar for the normal epithelial tissue. This break point in the slope is the result of the disorder/order transition in the conformation of the methylene chains in the lipids. The higher break point pressure in the malignant tissue indicates that a higher pressure is required to order the methylene chains and thus the conformational structure of the methylene chain at atmospheric pressure is more disordered in the malignant tissue than in the normal epithelial tissue.

Figure 9:
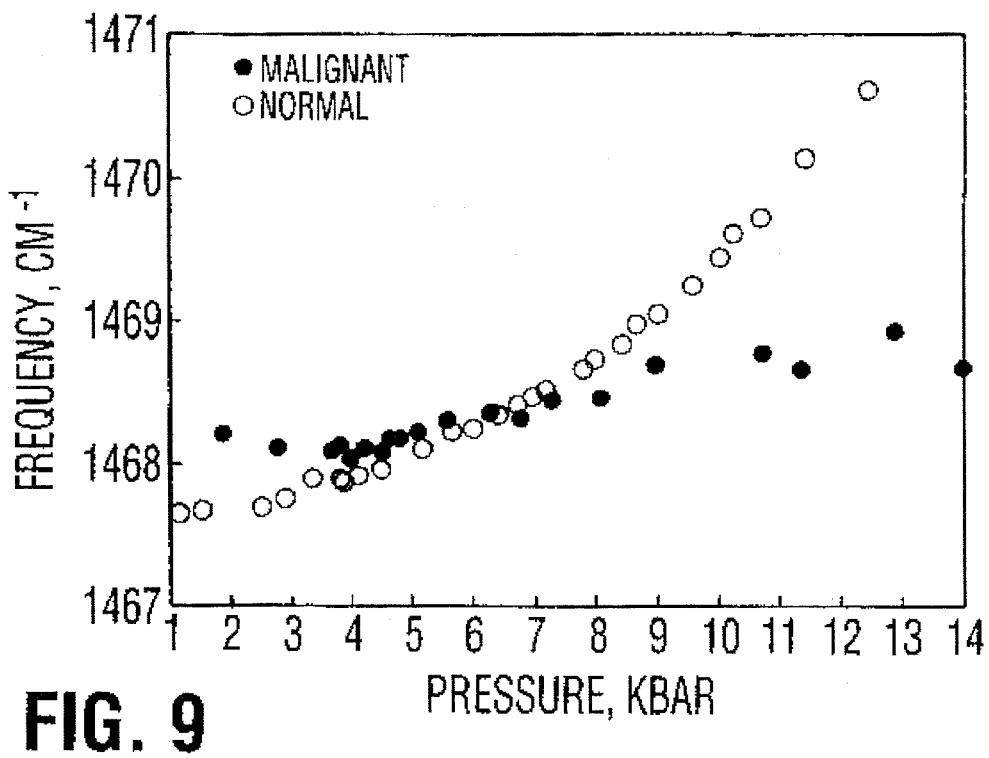
FIG. 9 shows the pressure dependencies of the $CH_2$ banding frequencies of the malignant and normal epithelial tissues.

FIG. 9 shows the pressure dependencies of the frequencies of the $CH_2$ bending mode of the malignant tissue and the normal epithelial tissue. As indicated by the break point in FIG. 8, the conformational structure of the methylene chains becomes ordered above 5 kbar in both the malignant and normal epithelial tissues. However, the methylene chains sill remain disordered at this pressure due to the large angle reorientational fluctuations and the twisting/torsion motions. Pressure is known to dampen the reorientational fluctuations and remove the twisting/torsion motions. At high enough pressure, these orientational motions will be removed and the frequency of the $CH_2$ bending mode will increase due to the enhanced interactions among neighboring ordered chains. This pressure induced frequency shift is much smaller in the malignant tissue than in the normal epithelial tissue. These results imply that higher pressure is required to achieve order in the lipids of the malignant tissue and thus the orientation of the methylene chains in membrane lipids is more disordered at atmospheric pressure in the malignant tissue than in the normal epithelial tissues. This change in the orientational order/disorder properties in the malignant colonic tissues have also been observed in the malignant cervical tissues.

Figure 10:
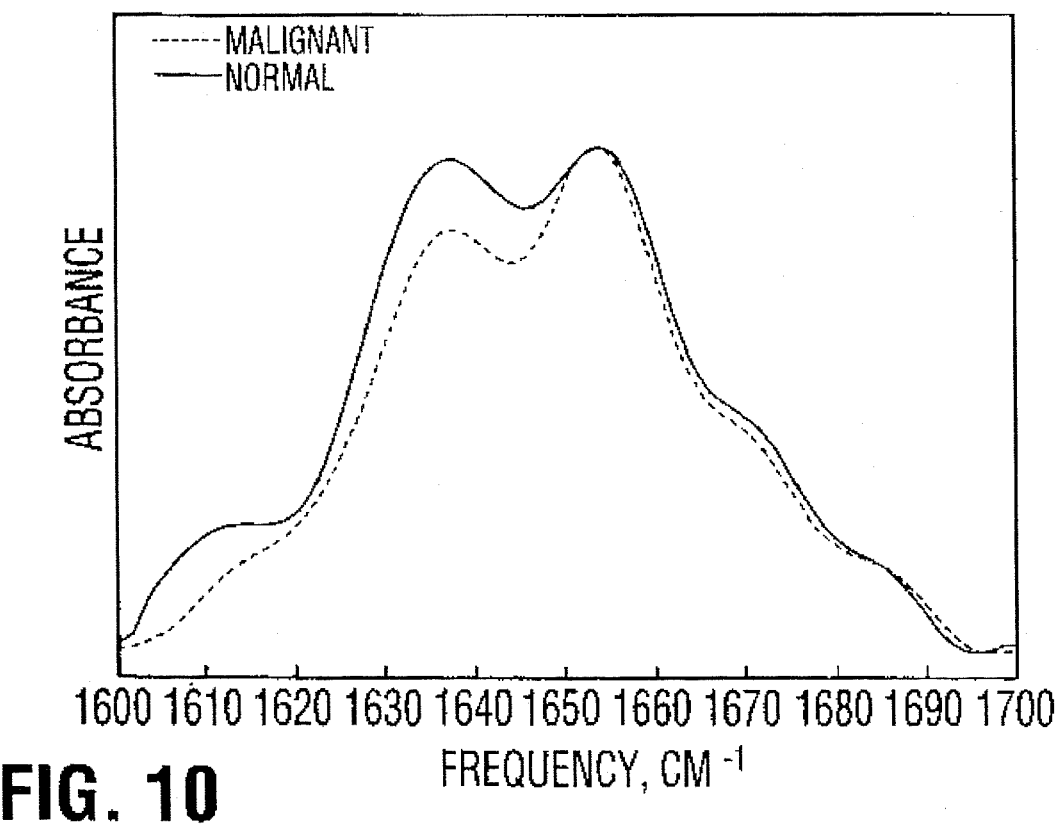
FIG. 10 shows the deconvolved infrared spectra in the amide I band region of the malignant and normal epithelial tissues with an enhancement factor of 1.6 and a band width of 20 $cm^{-1}$.

FIG. 10 compares the deconvolved amide I band spectra of the entire population of cellular proteins in the malignant and the normal epithelial tissues. These two spectra are very similar and exhibit two strong maxima at 1637 and 1654 $cm^{-1}$ corresponding to the β-sheet and the α-helix substructures, respectively. Therefore, the conformational substructures in the cellular proteins are dominated by the α-helix and the β-sheet with few unordered turns (1672 $cm^{-1}$). However, the ratio between the β-sheet segments and the α-helix segments in the proteins becomes smaller in the malignant tissue as indicated by the decrease in the intensity ratio between the 1637 $cm^{-1}$ and the 1654 $cm^{-1}$ band. The decrease in the intensity of the 1612 $cm^{-1}$ band in the malignant tissue indicates the reduction of the intermolecular hydrogen-bond aggregation between neighboring protein molecules in the malignant transformation.

Normal colonic mucosa consists of glandular epithelium and connective tissue. The connective tissue contains mainly the extracellular matrix composed of protein fibers, ground substance and tissue fluid. Connective tissue cells are embedded within this matrix. Because of such differences in the compositions between these two type of colonic tissues, their infrared spectra are expected to be different. This has already been evident from the spectra shown in FIGS. 1–4. While the infrared spectrum of the connective tissue in the frequency region 1200–1500 $cm^{-1}$ is comparable to that of the collagen proteins, many fine features in other regions of the spectra of the connective tissue are significantly different from those in the spectra of the collagen proteins and the epithelial tissue, for instance, the CH stretching region (2820–3030 cm$^{-1}$), the C-O stretching region (1140–1185 cm$^{-1}$), and the amide I band region (1600–1700 cm$^{-1}$).

As shown in FIG. 3, the intensity ratio between the methyl stretching band (2959 cm$^{-1}$) and the methylene stretching band (2853 cm$^{-1}$) is much higher in the connective tissue than in the epithelial tissue. The frequency of the symmetric CH$_2$ stretching band is lower in the connective tissue than in the epithelial tissue. The disorder/order transition takes place slightly below 3 kbar in the connective tissue and slightly above 3 kbar in the epithelial tissue as indicated by the changes in the slope of the pressure dependence of the symmetric CH$_2$ stretching frequency (FIG. 8). These results suggest that the conformational structure of the methylene chains in the membrane lipids is more disordered in the connective tissue than in the epithelial tissue.

Figure 11:
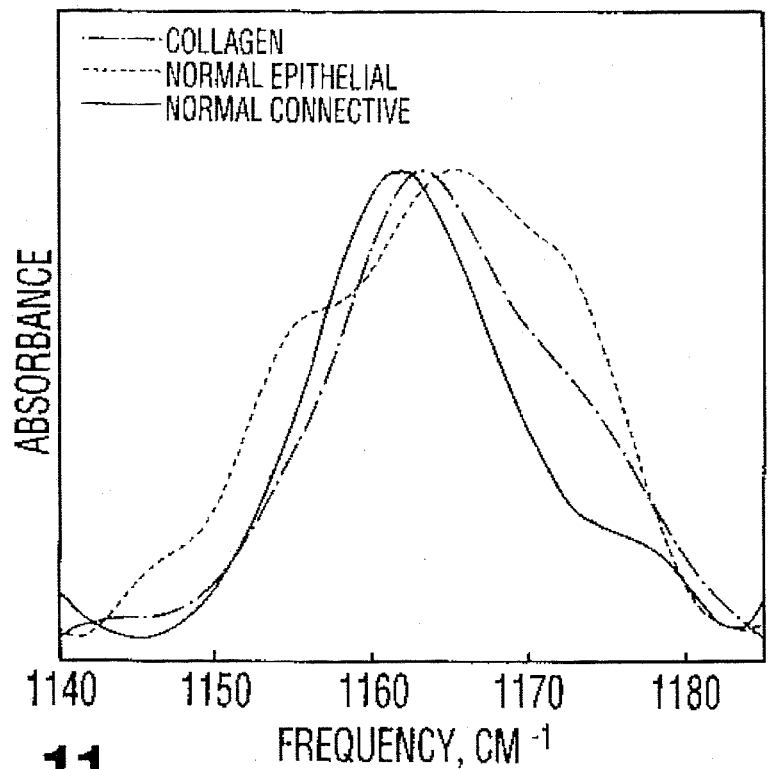
FIG. 11 shows the infrared spectra in the C-O stretching region of the epithelial tissue, the connective tissues and the type I collagen.

The infrared spectrum of the connective tissue in the C-O stretching region consists of a relatively narrow and symmetric band at 1162 cm$^{-1}$ with a weak shoulder at ~1173 cm$^{-1}$ (FIG. 11). In the same spectral region, there are three overlapping bands at 1155, 1165 and 1173 cm$^{-1}$ in the spectra of the epithelial tissue. The 1162 cm$^{-1}$ band in the connective tissue corresponds to the 1 165 cm$^{-1}$ band in the epithelial tissue and is due to the stretching mode of the hydrogen bonded C-O groups in the tissue proteins. The decrease in the frequency of this band in the connective tissue suggests that the strength of the hydrogen-bonds on these C-O groups is stronger in the connective tissue than in the epithelial tissue. The 1155 cm$^{-1}$ band of the hydrogen-bonded C-O groups from carbohydrates is not detected in the spectrum of the connective tissue. The 1173 cm$^{-1}$ band of the non-hydrogen-bonded C-O groups from the tissue protein is very weak in the connective tissue. The shape and the intensity distribution of the C-O bands in the connective tissue are significantly different from those in the collagen proteins. The 1162 cm$^{-1}$ band shifts to higher frequency and the intensity of the 1173 cm$^{-1}$ band becomes higher in the spectrum of collagen.

Figure 12:
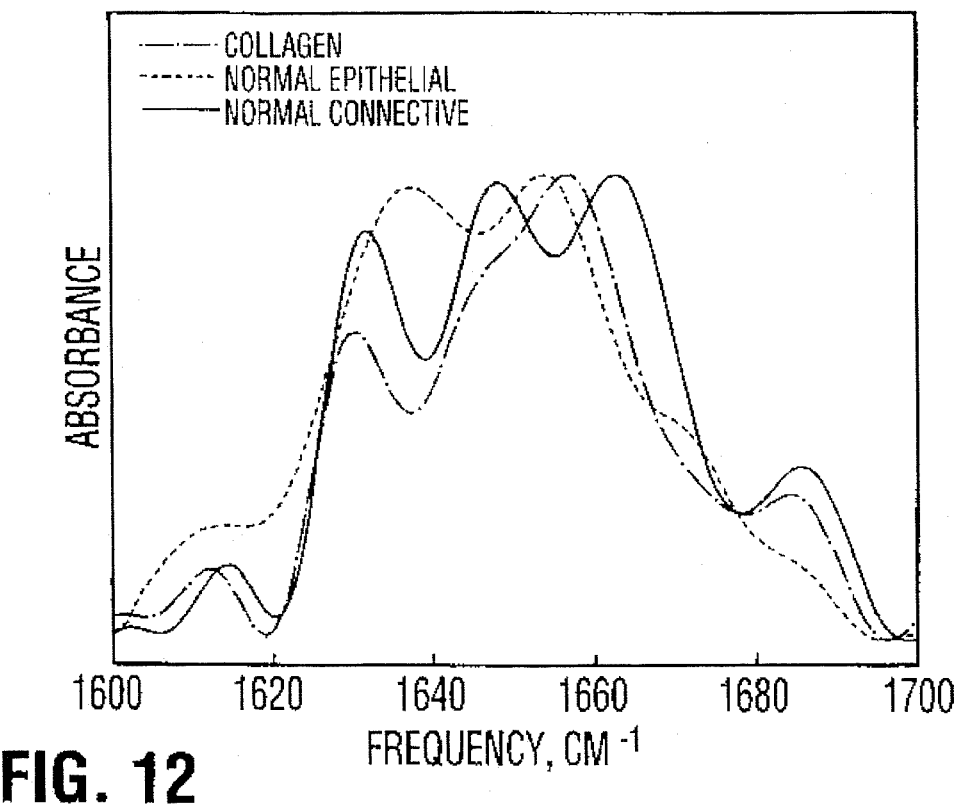
FIG. 12 shows the deconvolved infrared spectra in the amide I band region of the epithelial tissue, the connective tissue and the type I collagen with an enhancement factor of 1.6 and a band width of 20 $cm^{-1}$.

As shown by the deconvolved amide I band spectra in FIG. 12, the conformational substructures of the tissue proteins in the connective tissue are significantly different from those in either the epithelial tissue or the collagen. The conformational substructures in the connective tissue are dominated by the unordered random coils(1648 cm$^{-1}$ band) and turns (1663 cm$^{-1}$ band)) with some β-sheet (1632 and 1686 cm$^{-1}$ bands), whereas those in both the epithelial tissue and collagen are mainly contributed by α-helix and β-sheet. It is important to note that the conformational substructures in the connective tissue of the colon are significantly different from those in the connective tissue of the cervix. This may be due to the presence of many more lymphoid elements in the colonic lamina propria than in the connective tissue of the cervix. The frequency of the β-sheet band in the connective tissue is about 5 cm–1 lower than in the epithelial tissue, which indicates that the hydrogen-bond strength of the β-sheet segments in the connective tissue is stronger than in the epithelial tissue.

Despite the complexity of the human body, it is composed of only four basic types of tissue: epithelial, connective, muscular, and nervous. These tissues are associated with one another in various proportions to form different organs and systems of the body. The present results show that different tissue types give rise to different infrared spectra. Consequently, the infrared spectra of an organ tissue varies depending upon which part of the organ the tissue sample is taken or whether the tissue sample is contaminated with other types of tissues. Therefore, when FT-IR (Fourier Transform Infrared) spectroscopy is applied to investigate human tissues and their structural properties at the molecular level, well-defined tissue samples are required.

The colonic mucosa consists of glandular epithelium and lamina propria which is a loose connective tissue. As shown, infrared spectra of the colon epithelium and the lamina propria exhibit entirely different patterns and their pressure dependencies are not the same. Moreover, tissues of the same type from different organs also exhibit different infrared spectra. Therefore, pressure-tuning FT-IR spectroscopy is a powerful technique for the tissue identification if the infrared spectroscopic patterns of various types of human tissues are established and their pressure dependence are systematically examined.

It is well established that pressure-tuning infrared spectroscopy is very powerful for the study of cell anomalies at the molecular level in intact tissues and whole cells. However, this technique must be used properly when it is applied to investigate the structural changes in the cellular molecules in the pathway of carcinogenesis. For instance, in the study of colonic cancer the comparison of the pressure-tuning infrared spectra must be made between the malignant tumor and the normal epithelium rather than the mucosa of the colon, since colon cancer is mainly developed from the colonic epithelium. The following important structural changes at the molecular level in going from the normal epithelium to malignant tumor in the colon have been derived form the spectroscopic features: (1) increase in the number of hydrogen bonds on the phosphodiester groups in DNA, (2) a tighter intermolecular packing of nucleic acids, (3) decrease in the number of hydrogen-bonds on the C-OH groups of carbohydrates and proteins as a result of phosphorylation, (4) increase in the degree of both the conformational and orientational disorder of the methylene chains in membrane lipids,(5) decrease in the β-sheet/α-helix ratio of the conformational substructure in the tissue proteins, and (6) reduction in the intermolecular aggregation of the tissue proteins. Most of these structural changes at the molecular level in the colon are comparable with other malignant tumors.

The infrared spectra are significantly different among the epithelium, the lamina propria and the mucosa of the colon. The infrared spectra of these three types of normal tissues also differ from the spectra of the malignant colon tissue. These results mean that infrared spectroscopy can be applied for the detection of colon cancer from biopsies or for the determination of surgical margin in the resection for colorectal cancer. Tissue samples are obtained by either endoscopy or resection. The normal tissue samples thus obtained are not necessary pure normal epithelium and they may be pure lamina propria or both. Since the infrared patterns of these different types of normal tissues are not the same, the biopsy which shows any of these three infrared patterns can be unambiguously diagnosed as negative and distinguished from malignancy.

So far the results obtained from colon tissue have been described. Further experiments were carried out to measure the infrared spectra as a function of pressure of exfoliated cervical cells from 498 women. The spectra of the normal women exhibited dramatic differences from those obtained from patients with either cancer or the precancerous condition called dysplasia. It was found that a number of structural and other cellular changes at the molecular level associated with cervical cancer were responsible for the different infrared spectra. Such findings confirm the view that that recording of infrared spectra from exfoliated cervical cells may be of diagnostic value.

Exfoliated cervical cells are commonly obtained by scraping or brushing from the surface of the normal epithelial tissues, or tumors of the cervix. Below the normal epithelial tissue is the connective tissue, which provides a matrix that serves to connect and bind the cells and organs and ultimately give support to the body, Unlike the other tissue types that are formed mainly by cells, the major constituent of connective tissue is its extracellular matrix, composed of protein fibers, an amorphous ground substance, and tissue fluid. Embedded within the extracellular matrix are the connective tissue cells. Therefore, the infrared spectrum of the normal connective tissue of the cervix is expected to be different from that of the normal epithelial tissue or the exfoliated normal cells of the cervix.

Infrared spectra of the normal epithelial and connective tissues as well as the malignant tumor tissues of human cervix were measured and analyzed. The infrared spectra of the normal connective tissue differs considerably from those of the normal epithelial and of the malignant tissues. The infrared spectra of the normal and the malignant epithelial tissues resemble those of the corresponding exfoliated cells.

Cervical tissue samples of seven patients were obtained at the Ottawa General Hospital. From each patient, samples were obtained from both the tumor itself and the normal tissue 2 cm away from the tumor. All the samples were stored at −80° C. until used. Each tissue sample was cut into two segments. One was used for spectroscopic studies. From the other, 5 −µm thick microtone sections were out. These sections were fixed, stained, and examined histologically. The normal connective tissue samples were obtained by removing the epithelial layer of each sample under the microscope and then rinsing with saline solution.

Infrared spectra were recorded on a Digilab FTS-40A Fourier transform spectrometer equipped with a liquid nitrogen-cooled mercury-cadmium-telluride detector. For each spectrum, a total of 512 scans at 4 $cm^{-1}$ resolution were co-added. Small amounts (typically 0.1 mg) of tissue sections were placed at room temperature, together with powdered α-quartz, into a 0.63-mm-diameter hole in a 0.23-mm-thick stainless steel gasket mounted on a diamond anvil cell. Pressure at the sample was determined from the 695-$cm^{-1}$ infrared absorption band of α-quartz. Infrared spectra of at least five different parts of each sample were also recorded at atmospheric pressure with a specially designed infrared cell. These spectra were used to examine the tissue distribution in each sample and also the reproducibility of the spectra.

Figure 13:
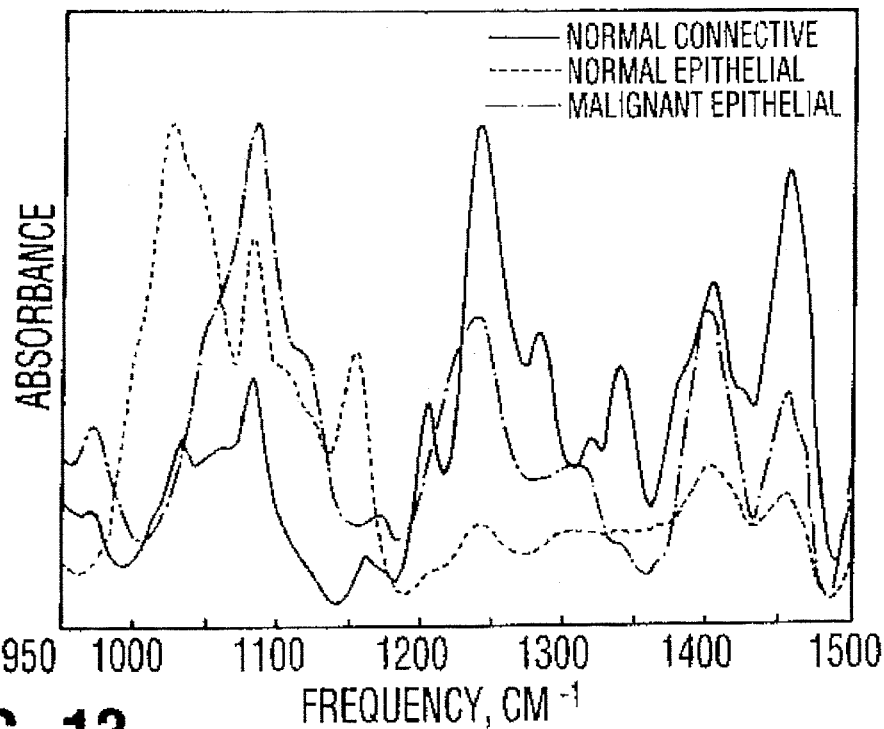
FIG. 13 shows the infrared spectra of cervical tissues in the frequency region 950 to 1500 $cm^{-1}$.

Infrared spectra of the normal connective, the normal epithelial, and the malignant epithelial tissues of human cervix were measured as a function of hydrostatic pressure. All these spectra are reproducible among tissue samples from seven patients. The representative infrared spectra in the frequency region 950 to 1500 $cm^{-1}$ of the normal epithelial and the malignant epithelial tissues are compared in FIG. 13. The features in the spectra of these cervical tissue samples are almost identical to those in the spectra of the corresponding exfoliated cervical cells. For instance, changes in the intensity of the glycogen bands at 1025 and 1047 $cm^{-1}$ the phosphodiester band at 1082 and 1240 $cm^{-1}$ the C-O stretching band at 1155 $cm^{-1}$ and the bands at 1303 and 970 $cm^{-1}$ that are observed in the spectrum of the exfoliated malignant cervical cells are also observed in the spectrum of the malignant cervical tissue. The infrared spectrum in the same frequency region of the normal connective tissue of human cervix is also compared with that of the normal epithelial tissue in FIG. 13. Considerable differences in the spectra between these two types of normal tissues of human cervix are evident from the FIG. 13. The glycogen bands at 1025 and 1047 $cm^{-1}$ have almost disappeared in the spectrum of the normal connective tissue. The decrease in the intensities of the glycogen bands in the normal connective tissue is also observed in the spectrum of the malignant epithelial tissue. However, the infrared feature of the normal connective tissue in the frequency region above 1150 $cm^{-1}$ are significantly different from those in the malignant epithelial tissue (FIG. 13). Sharp bands at 1204, 1283, 1318, and 1239 $cm^{-1}$ in the spectrum of the normal connective tissue are not observed in the spectra of either the normal or the malignant epithelial tissues. The intensity distribution among all the infrared bands in the spectrum of the normal connective tissue is entirely different from that in the normal and malignant epithelial tissues.

Figure 14:
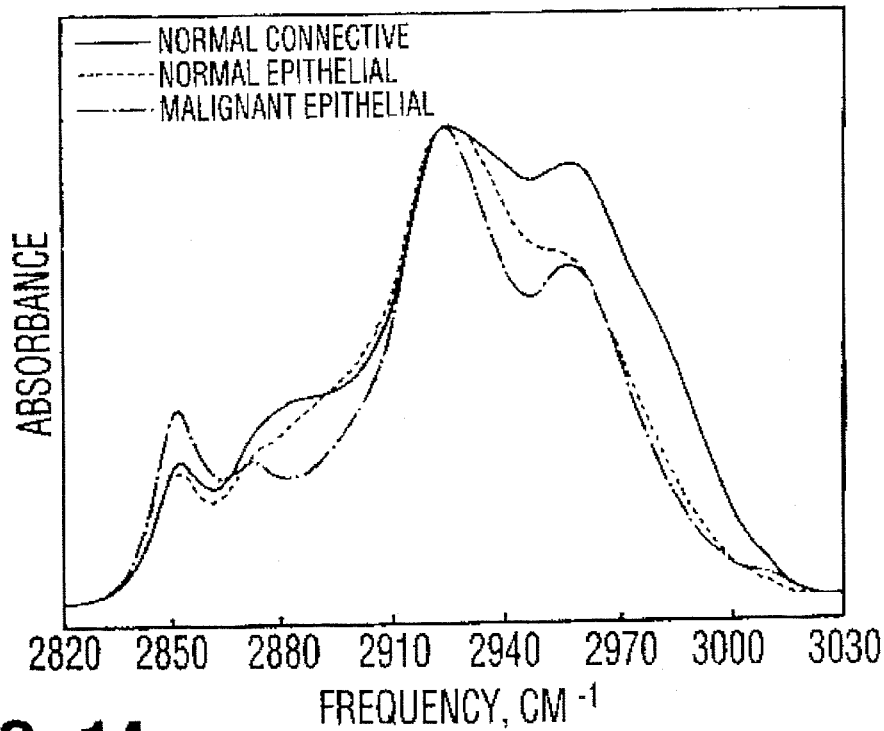
FIG. 14 shows the infrared spectra of cervical tissues in the frequency region 2820 to 3030 $cm^{-1}$.
Figure 15:
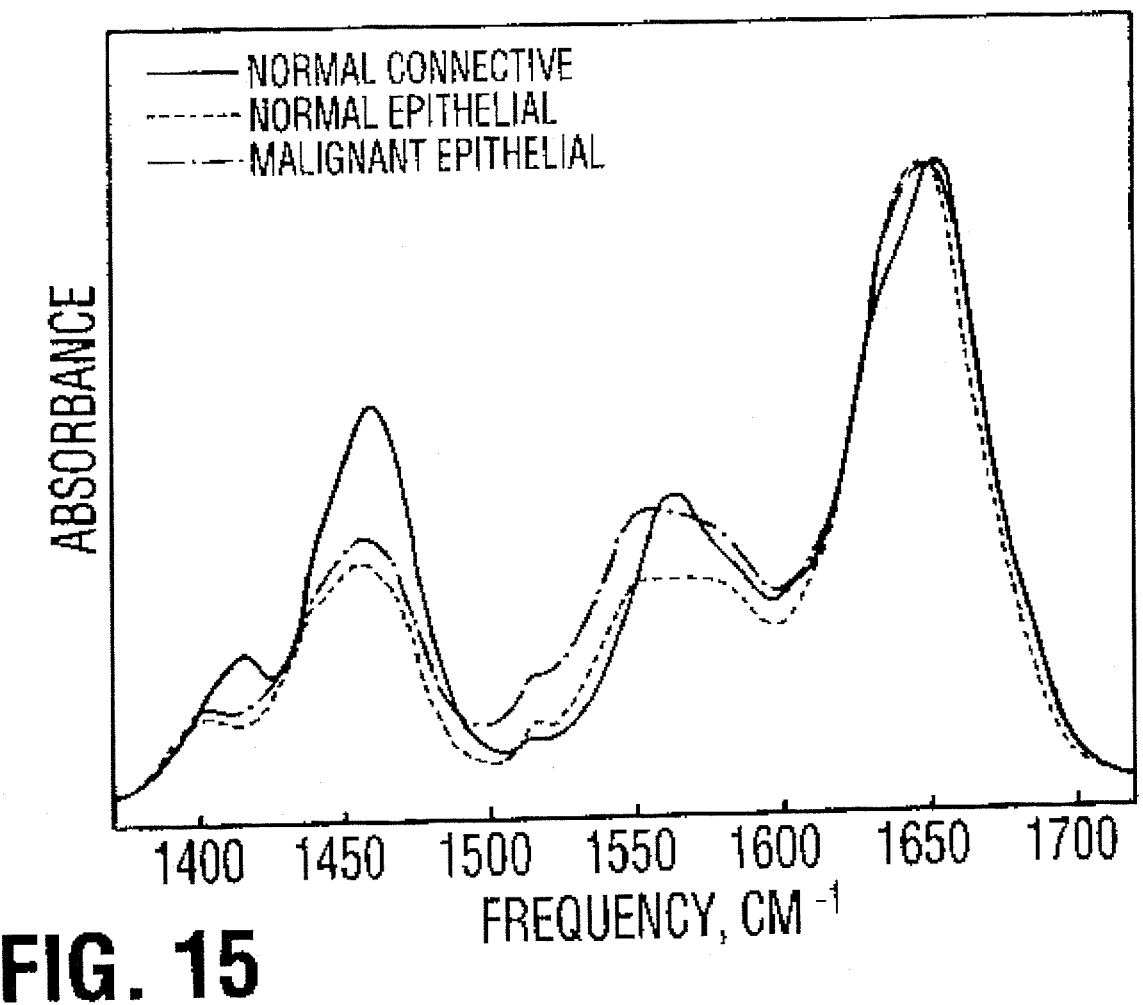
FIG. 15 shows the infrared spectra of cervical tissues in the frequency region 1370 to 1720 $cm^{-1}$.

FIG. 14 shows the infrared spectra in the frequency region 2820 to 3030 $cm^{-1}$ of the normal connective, the normal epithelial, and the malignant epithelial tissues. The bands at 2852 and 2957 $cm^{-1}$ are due to the CH stretching modes of the methylene and methyl groups, respectively. The peak intensity ratio between the methyl band and the methylene band decreases in the malignant cervical tissue (FIG. 14). The decrease in this intensity ratio is also observed in other malignant cells and tissues. The intensity of the methylene stretching band is about the same between the normal epithelial and the normal connective tissues, while the intensity of the methyl band of the normal connective tissue is much higher than that of the normal epithelial tissue. The 2957-$cm^{-1}$ methyl stretching band is contributed by the methyl groups in membrane lipids, proteins, and other component molecules in these tissues. As mentioned earlier in the introduction, normal connective tissues contain a large amount of protein fibers. Thus, the strong methyl band in the normal connective tissue compared with the normal and malignant epithelial tissues may be the result of the presence of a large number of methyl groups in these protein fibers, FIG. 15 shows the representative infrared spectra of the three types of cervical tissues in the frequency region 1370 to 1720 $cm^{-1}$. The bands near 1650 and 1550 $cm^{-1}$ are mainly due to the amide I and amide II vibrational modes of tissue proteins, respectively, which provide information concerning the conformational substructures in tissue proteins. FIG. 15 shows that both the amide I and amide II bands of the normal connective tissue are significantly different from those of the normal and the malignant epithelial tissues.

All the infrared spectra in FIGS. 13 to 15 are the original spectra without smoothing or other data treatment. However, noise, interference fringes, and water vapor bands are hardly detectable in these spectra. These infrared spectra of human cervical are of extremely high quality.

Several structural changes at the molecular level among the normal connective, the normal epithelial, and the malignant epithelial cervical tissues have been extracted from their infrared spectra in the following spectral regions: (1) phosphodiester stretching regions (1080–1086 $cm^{-1}$ and 1190–1270 $cm^{-1}$), (2) C-O stretching region (1140–1185 $cm^{-}$), (3) $CH_2$ bending region (1464–1476 $cm^{31\ 1}$) and (4) amide I mode region (1600–1700 $cm^{-1}$).

Figure 16:
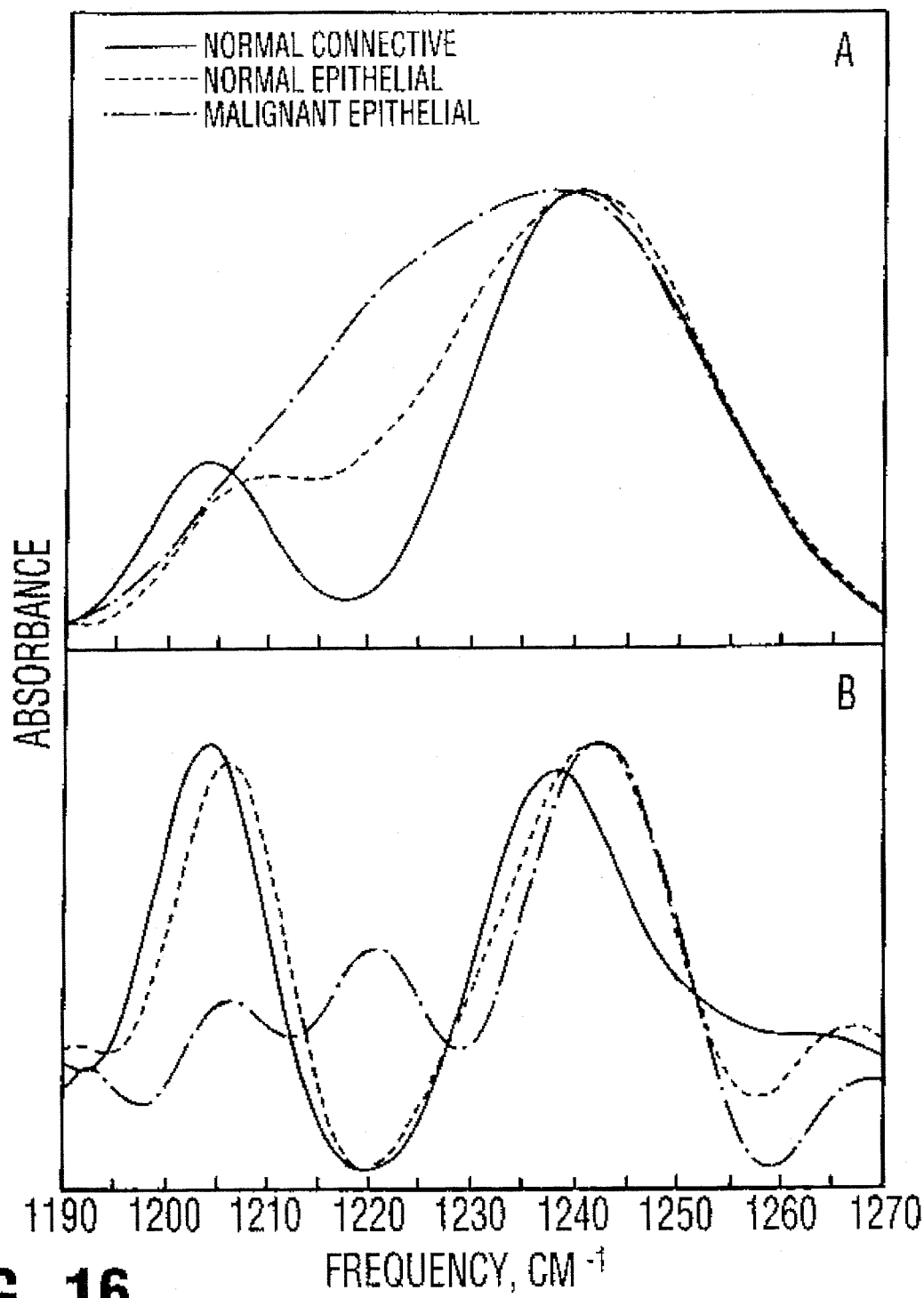
FIG. 16 shows the infrared spectra of cervical tissues in the asymmetric phosphate stretching region. (A) Superimposed original spectra from three types of cervical tissues. (B) Corresponding third-power derivative spectra with a break point 0.3.

The representative infrared spectra of the antisymmetric phosphate stretching mode of the normal connective, the normal epithelial, and the malignant epithelial tissues are enlarged and shown in FIG. 16, part A. Corresponding third-power derivative spectra are shown in FIG. 16, part B. This phosphate band in the infrared spectra of tissues and cells is mainly due to the antisymmetric stretching vibration of the Phosphodiester groups in nucleic acids. As in the case of exfoliated malignant cells, this band of the malignant cervical tissue is much broader than that of the normal tissue and consists of two overlapping bands with Peak positions at 1221 and 1242 cm$^{-1}$. The frequency of this band is very sensitive to the interaction between water molecules and the phosphodiester groups in nucleic acids. This band is normally at about 1240 cm$^{-1}$, but its frequency shifts to about 1220 cm$^{-1}$ when the phosphodiester groups are fully hydrogen-bonded to water molecules. This frequency shift as a result of the formation of hydrogen bonds on the phosphodiester group was further confirmed by a pressure tuning infrared spectroscopic study of the exfoliated cervical cells. The dramatic increase in the intensity of the 1220-cm$^{-1}$ component band in the malignant epithelial tissue indicates that a large number of phosphodiester groups in the malignant cells become hydrogen bonded to water molecules. The antisymmetric phosphate stretching band of the normal connective tissue is a single and relatively narrow band and is comparable with that of the normal epithelial tissue (FIG. 16). However, the peak position of this band of the normal connective tissue is about 4 cm$^{-1}$ lower than that of the normal epithelial tissue.

Figure 17:
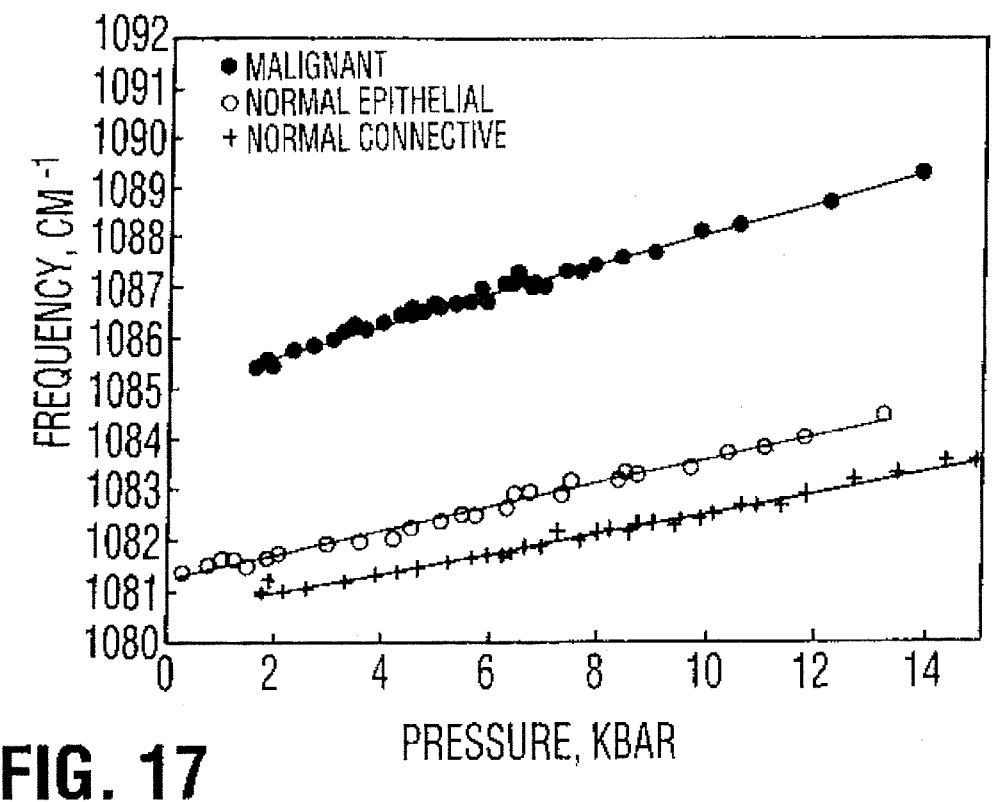
FIG. 17 shows the pressure dependencies of the symmetric phosphate stretching frequency of cervical tissues.

Pressure dependencies of the symmetric phosphate stretching frequencies of the three types of cervical tissues are shown in FIG. 17. This symmetric phosphate stretching band is mainly from the phosphodiester groups in nucleic acids. The frequency of this band increases linearly within the experimental error with increasing pressure in all three tissues. The pressure dependence of this frequency is, however, slightly different among these three types of tissues. They are 0.30, 0.24, and 0.20 cm$^{-1}$/kbar for the malignant epithelial, the normal connective, and the normal epithelial tissues, respectively. The frequency of this band is about 4 cm$^{-1}$ higher in the malignant tissue than in the normal tissue, indicating that the intermolecular interaction among nucleic acids is stronger and thus the intermolecular packing is tighter in the malignant tissue. This observation is most likely the result of hydrogen bondings between the nucleic acids and water molecules in the malignant tissue. This hydrogen-bond formation partially neutralizes the negative charge on the phosphate after groups of nucleic acids and thus reduces the repulsion force between neighboring nucleic acid molecules. Consequently, the intermolecular packing between neighboring nucleic acids becomes tighter. The frequency of this band in the normal connective tissue is only slightly higher than that in the normal epithelial tissue. The magnitude of the pressure shift of this frequency among the three types of cervical tissues is proportional to their original frequencies at atmospheric pressure. For instance, the frequency of the malignant epithelial tissue is the highest at atmospheric pressure, and the pressure effect on this frequency of the malignant epithelial tissue is the strongest (FIG. 17). This result implies that the pressure-enhanced intermolecular interaction is stronger for the tissue with more closely packed nucleic acids.

Figure 18:
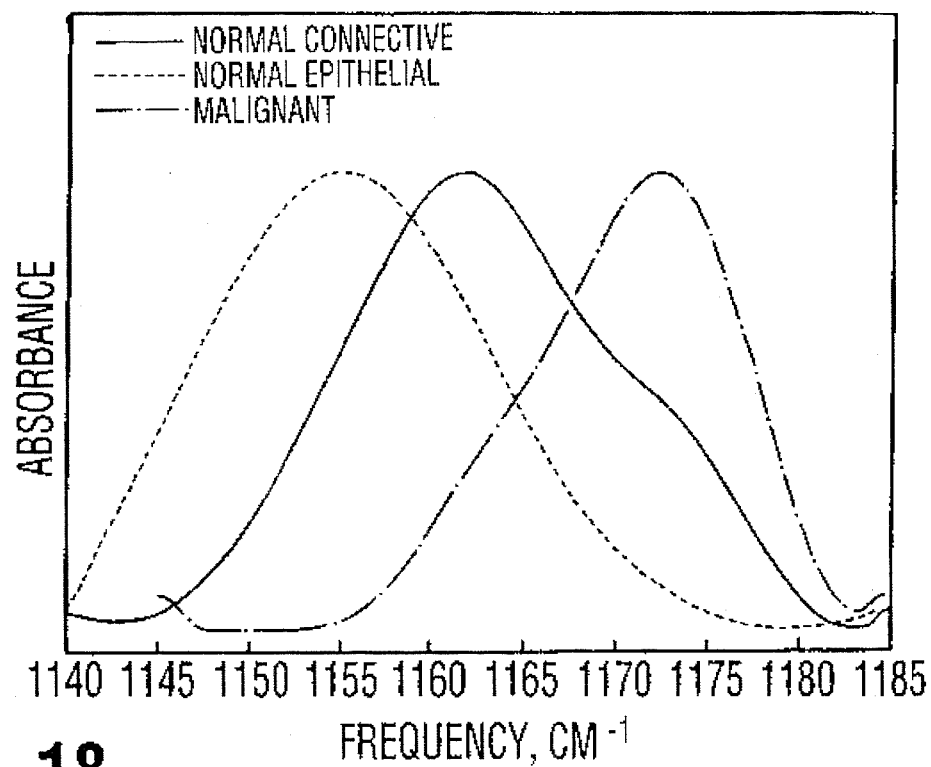
FIG. 18 shows the superimposed infrared spectra in the C-O stretching region from three types of cervical tissues.

FIG. 18 shows the infrared spectra of the C-O stretching bands of the cervical tissues. The C-O stretching bands of the normal and the malignant epithelial tissues are about the same as those of the corresponding normal and malignant cervical cells observed previously. They consist of three overlapping bands at 1155, 1162, and 1172 cm$^{-1}$, respectively. The intensities of the first two bands at 1156 and 1172 cm$^{-1}$ decrease while that of the 1172-cm$^{-1}$ band increases in the spectrum of the malignant epithelial tissue compared with the normal epithelial tissue. The 1155-cm$^{-1}$ band is due to the C-O stretching mode of glycogen, whereas those at 1162 and 1172 cm$^{-1}$ are mainly due to the C-O stretching modes of the C-OH groups of serine, threonine, and tyrosine of proteins. These two protein C-O stretching bands have been observed in the spectra of colon cells and other tissues and cells. The component bands at 1155 and 1162 cm$^{-1}$ arise from the stretching modes of hydrogen-bonded C-O groups, whereas the band at 1172 cm$^{-1}$ is due to the stretching mode of non-hydrogen-bonded C-O groups. The dramatic decrease in the intensities of the two low-frequency component bands at 1155 and 1162 cm$^{-1}$ in the malignant tissue and cells of cervix (FIG. 18) suggest that in cervical cancer the glycogen level is extremely low and most of the hydrogen bonds on the C-O groups of cellular proteins have disappeared. The lack of the hydrogen-bonded C-O groups in the cellular proteins of cancer may be the result of phosphorylation of the C-OH groups, which is an important event in carcinogenesis. In the process of phosphorylation, the OH groups are replaced by the larger phosphate groups. Thus, water molecules are driven away from the C-O groups by the steric hindrance effect of the phosphate groups, As evident from FIG. 18, both the band shape and peak position of the C-O stretching band of the normal connective tissue are different from those of the normal and malignant epithelial tissues. The intensities of both the 1155-cm$^{-1}$ and the 1172-cm$^{-1}$ component bands are extremely low in the connective tissue, indicating that the level of glycogen is low and the majority of the C-OH groups in the cellular proteins are hydrogen-bonded.

Figure 19:
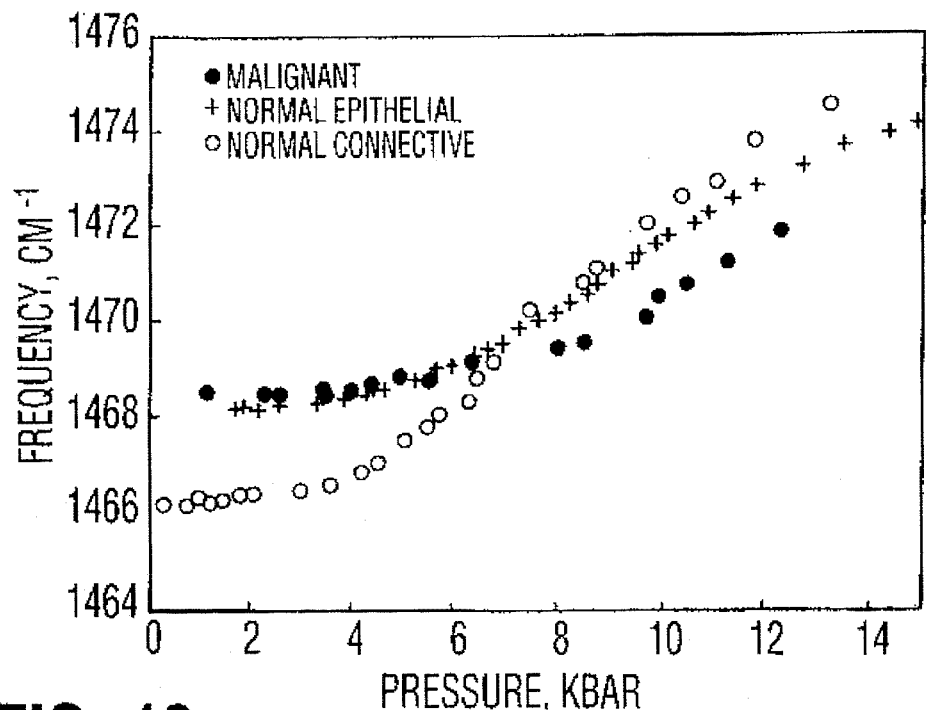
FIG. 19 shows the pressure dependencies of the bending mode frequency of the methylene chain of lipids of cervical tissues.

FIG. 19 shows the pressure dependencies of the CH$_2$ bending frequencies of the methylene chains of lipids in the cervical tissues. The pressure-induced frequency shifts of this vibrational mode in the malignant and the normal epithelial cervical tissues observed comparable with those previously observed in the corresponding exfoliated cells of cervix. The smaller pressure shift of this frequency in the malignant samples has been attributed to the fact that the conformational and orientational structure of the methylene chains in membrane lipids is more disordered in cervical cancer than in the normal cervical specimens. The frequency of this CH$_2$ bending mode and its pressure behavior in the normal connective tissue are considerably different from those in the normal and malignant epithelial tissues (FIG. 19), but resemble those observed in the accumulated lipids in liver tissues of mice.

Figure 20:
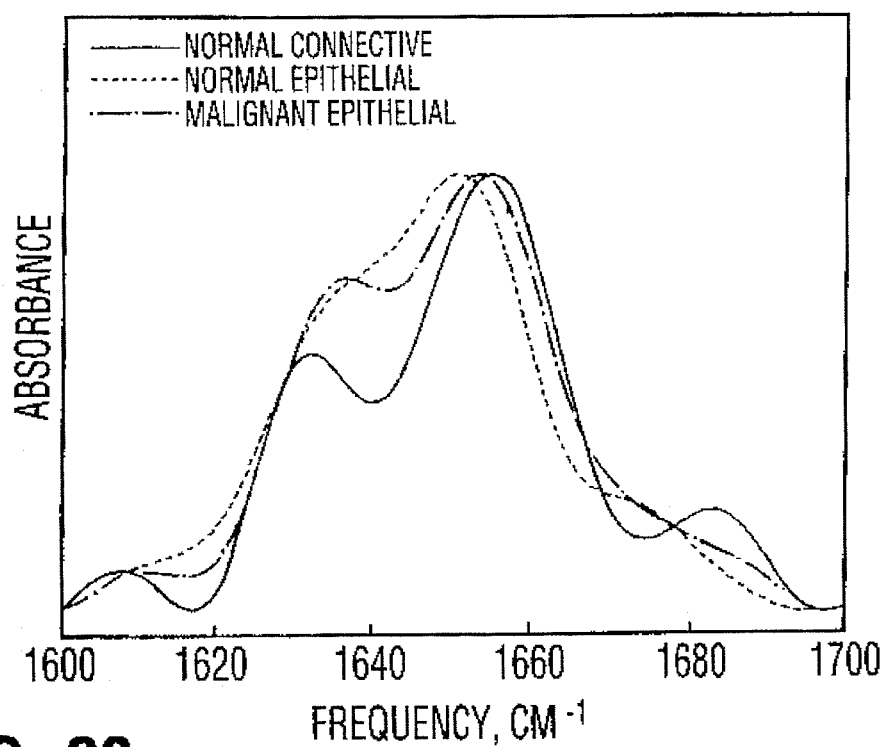
FIG. 20 shows the deconvolved infrared spectra in the amide I band region of cervical tissues with an enhancement factor of 1.4 and a band width of 20 $cm^{-1}$.

FIG. 20 compares the deconvolved amide I band spectra of the entire population of cellular proteins in the malignant epithelial, the normal epithelial, and the normal connective cervix tissues. The amide I band of proteins is due to the in-plane C-O stretching vibration weakly coupled with C-N stretching and in-plane N-H bending of the amide groups in proteins. The peak maximum of the amide I band is insensitive to the secondary structure in proteins. The α-helical structure has its peak maximum near 1653 cm$^{-1}$, the parallel β-sheet near 1635 cm$^{-1}$ and the antiparallel β-sheet near 1683 cm$^{-1}$. The amide I band of unordered random coils and turns are at around 1645 cm$^{-1}$ and 1665 cm$^{-1}$, respectively. The band near 1611 cm$^{-1}$ is due to the amide I mode of the intermolecular amide groups in which the hydrogen bonds are formed between neighboring protein molecules. The intensity of this band is a measure of the magnitude of intermolecular aggregation in proteins. Since each globular protein molecule contains segments with different substructures, the amide I band of globular proteins usually appears as a broad band with several maxima. The changes in the relative intensities of these maxima can be used to monitor changes in the secondary substructures of globular proteins.

It is evident from the spectra of the amide I mode in FIG. 20 that the conformational structure of the overall proteins in all the three types of cervical tissues is dominated by the α-helical structure with considerable segments of β-sheet, However, as indicated by the relative intensity of the component bands in FIG. 20. the β-sheet. to-α-helix ratio decreases considerably in the normal connective tissue. The frequency of the α-helical band increases in the order of the normal epithelial, the malignant epithelial, and the normal connective tissues, whereas that of the β-sheet band decreases in the same order. Therefore, the strength of the hydrogen bonds on the amide groups of the α-helical segments decreases while that of the β-sheet segments in tissue proteins increases in the order of the normal epithelial, the malignant epithelial, and the normal connective tissues.

The component band of the intermolecular amide groups at 1611 $cm^{-1}$ is relatively weak in all three types of cervical tissues. In the normal connective tissue this band increases slightly in intensity and shifts to 1608 $cm^{-1}$. These results indicate that the intermolecular hydrogen bonds are stronger and the protein aggregation increases in the normal connective tissue compared to the normal and the malignant epithelial tissues. There is a considerable amount of antiparallel β-sheet segments in the normal connective tissue proteins as indicated by the intensity of the 1683-$cm^{-1}$ band. The amount of anti-parallel β-sheet segments is minimum, whereas unordered turn structure (1673-$cm^{-1}$ band) becomes significant in the normal epithelial tissue. Therefore, the amide I bands in FIG. 20 demonstrate that the conformational substructures of the tissue proteins are significantly different among the three types of cervical tissues.

The infrared spectra of the normal epithelial and the malignant epithelial tissues of human cervix obtained above are almost the same as those of the corresponding exfoliated cells from normal and malignant cervical tissues. Eight of the important structural changes derived from spectroscopic features in the exfoliated malignant cells are also shared by the malignant cervical tissues—(1) the amount of glycogen is dramatically decreased in cancerous cervical tissue; (2) there is presence of extensive hydrogen bondings of the phosphodiester groups of nucleic acids; (3) the symmetric phosphate stretching band of the phosphodiester groups in nucleic acids at 1082 $cm^{-1}$ is shifted to 1086 $cm^{-1}$ in the malignant tissues, indicating a tighter packing of nucleic acids in the cervical cancer tissues; (4) the hydrogen bonding of the C-OH groups of carbohydrates and proteins is reduced in the malignant tissue as a result of the phosphorylation of these C-OH groups; (5) the degree of disorder of methylene chains of membrane lipids is increased, (6) an additional band peaking at 970 $cm^{-1}$ is observed in the malignant tissues; (7) the methyl-to-methylene ratio decreases significantly in cancer cells; and (8) the hydrogen-bond strength of the amide groups in the α-helical segments decreases while that in the β-sheet segments increases. This extensive set of common spectroscopic changes between the malignant tissue and exfoliated malignant cells of cervix strengthens the argument that the malignant cervical cells are responsible for most of the spectroscopic findings associated with cervical cancer.

The present data on tissues and the previous data on exfoliated cells show significant differences in many features among the infrared spectra of normal, dysplastic, and malignant cervical cells and tissue. Such findings suggest that the recording of infrared spectra of exfoliated cells and the biopsy of cervical tissue may be used in rapid evaluation of cervical cancer or as an adjunct for screening of large-volume normal cervical specimens. There are obvious advantages in using infrared spectroscopy over the present pathology method in screening and diagnosis. It is rapid, accurate, inexpensive, and automatable, and it requires a minimal amount of sample.

The infrared spectrum of the connective tissue of cervix in the frequency region 960 to 1100 $cm^{-1}$ is very similar to that of the malignant tissue and cells. In particular, the intensities of the glycogen bands at 1025 and 1047 $cm^{-1}$ are extremely low in both the normal connective tissue and the malignant tissue. Therefore, if only the infrared spectra in the glycogen region are examined for the normal cervical tissues or the exfoliated cells of normal cervix with some contamination of the connective tissue, these normal cervical specimens will be misinterpreted as malignant tissues and cells. Fortunately, as shown in FIG. 16, the infrared spectrum of the normal connective tissue in the frequency region 1200 to 1500 $cm^{-1}$ is significantly different from that of the malignant epithelial tissue. Several well-defined sharp bands at 1204, 1283, 13 18, and 1339 $cm^{-1}$ in the spectrum of the normal connective tissue are not observed in the spectrum of the malignant tissue. The intensities of the 1242., 1404-, and 1457-$cm^{-1}$ bands with respect to that of the 1082-$cm^{-1}$ band are much higher in the normal connective tissue than in the malignant tissue. Moreover, the intensity of the 1457-cm band is higher than that of the 1404-$cm^{-1}$ band in the normal connective tissue, whereas it is lower than that of the 1404-$cm^{-1}$ band in the malignant tissue. Therefore, the normal connective tissue can be differentiated unambiguously from the malignant tissue by examining the infrared spectra in the frequency region 1200 to 1500 $cm^{-1}$.

The infrared spectra of normal colon tissues observed above show features that resemble those in the infrared spectra of the normal connective tissues. All the normal colon tissue samples were the normal mucosa tissues obtained immediately after bowel resection. Mucosa tissues of colon consist of a layer of epithelial tissue and a layer of connective tissue. Therefore, the similarity between the spectra of the cervical connective tissues and the normal mucosa tissues of colon suggests that the features in the spectrum of the normal connective tissue of colon are about the same as those in the normal connective tissue of cervix.

The data also demonstrate that there are a number of advantages in infrared spectroscopy over other biochemical and biophysical methods in the study of human tissues and cells. First, the component molecules are examined in their natural state in the intact tissues and cells. Thus, their physical state and interactions with other molecules can be studied. For instance, the increase in the hydrogen bondings on the phosphodiester groups of nucleic acids in cancer could not be evaluated in isolated nucleic acids, since nucleic acids would be stripped of histones in the process of isolation and their structural properties would no longer be the same. Second, several component molecules can be monitored simultaneously. As shown above, the changes in amount, structure, and interactions of proteins, lipids, nucleic acids, and carbohydrates can be evaluated in a single tissue section. Third, only less than 0.1 milligram of unprocessed tissue sections or cells are needed.

Figure 21:
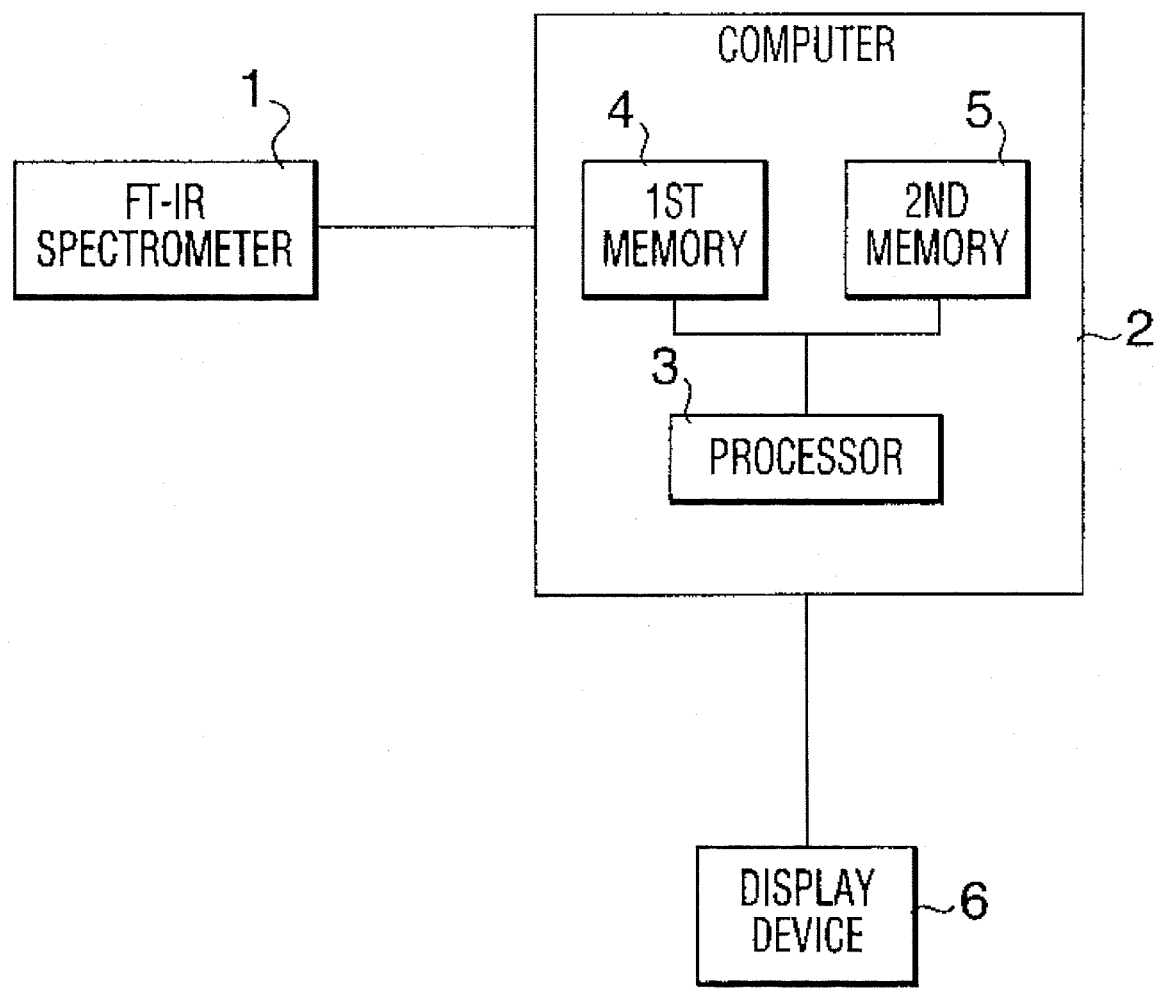
FIG. 21 is a block diagram of an apparatus for carrying out the invention.

The method described in above lends itself to automation. FIG. 21 shows schematically an apparatus for carrying out the invention, which comprises and FT-IR spectrometer 1 connected to a personal computer 2, including a central microprocessor 3 and first and second memories 4, 5. The latter can take the form of files on a standard hard disk, for example. The computer 2 is connected to display device 6, for example a CRT screen.

The pressure dependent infrared spectra of different types of human tissue are stored in first memory 4 as a library of known spectra. The infrared spectrum from a sample under test, as determined by the spectrometer 1, is then stored in memory 2. The computer 3 can then display the IR spectrum of the sample alongside those spectra stored in the first memory 4 on display device 6 for visual comparison, or alternatively can determine the best match on the basis of a predetermined algorithm so as to read out directly the most likely type of tissue.

When the apparatus is used for detecting malignancies, the computer 3 compares the infrared spectrum of the sample with the spectra for normal tissue, and if it finds a match is able to make an immediate negative determination of malignancy.

Although the invention has been described with reference to colon and cervical tissue, it is of course applicable to tissue from other organs. In accordance with the invention, the distinguishing spectra of the different types of tissue are used to form a library to permit fast subsequent identification.

The invention has been described with reference to humans, although it is of course applicable to animal tissue.

I claim:

1. A method of identifying tissue comprising the steps of determining the infrared spectrum of a tissue sample over a range of frequencies in at least one frequency band, and comparing the infrared spectrum of said sample with a library of stored infrared spectra of known tissue types by visual comparison or using pattern recognition techniques to find the closest match.

2. A method as claimed in claim 1, wherein said infrared spectra are determined by FT-IR spectroscopy.

3. A method as claimed in claim 1, wherein said infrared spectroscopy is carried out under pressure, and said infrared spectra include the pressure dependence thereof.

4. A method as claimed in claim 1, wherein said known tissue types are selected from the group consisting of: the colon epithelium, lamina propria, the cervical epithelium, and cervical connective tissue.

5. A method as claimed in claim 1, wherein the infrared spectra of said known tissue types are stored in a memory.

6. A method as claimed in claim 1, wherein said tissue is human tissue.

7. A method of identifying non-malignant tissue, comprising the steps of determining the infrared spectrum of a tissue sample over a range of frequencies in at least one frequency band; comparing said infrared spectrum with a library of infrared spectra of known normal tissue types by visual comparison or using pattern recognition techniques; and identifying the sample as non-malignant if it substantially matches one of said know tissue types.

8. A method as claimed in claim 7, wherein said infrared spectra are determined by FT-IR spectroscopy.

9. A method as claimed in claim 7, wherein said infrared spectroscopy is carried out under pressure, and said infrared spectra include the pressure dependence thereof.

10. A method as claimed in claim 7, wherein said tissue is human tissue.

11. An apparatus for identifying tissue comprising:

a) a first memory for storing the infrared spectra of a plurality of known tissue types in at least one frequency band;

b) an infrared spectrometer for determining the infrared spectrum of a tissue sample over a range of frequencies in at least one frequency band;

c) a second memory for storing said infrared spectrum of said tissue sample;

d) a processor for comparing the infrared spectra stored in said first and second memories using pattern recognition techniques to find the closest match; and e) a display device for displaying the results of said comparison to permit identification of said sample tissue.

12. An apparatus as claimed in claim 11, wherein said infrared spectrometer is an FT-IR spectrometer.

13. An apparatus as claimed in claim 11, wherein said infrared spectrometer is a pressure spectrometer, and the pressure dependence of said infrared spectra of said known tissue types are also stored in said first memory.

* * * * *